US008175692B2

(12) United States Patent  
Kimura et al.

(10) Patent No.: US 8,175,692 B2  
(45) Date of Patent: May 8, 2012

(54) ELECTROCARDIOGRAM SIGNAL-PROCESSING METHOD AND ELECTROCARDIOGRAM SIGNAL-PROCESSING DEVICE

(75) Inventors: Yoshitaka Kimura, Sendai (JP); Mitsuyuki Nakao, Sendai (JP); Shinichi Chida, Sendai (JP); Kunihiro Okamura, Sendai (JP); Michiyoshi Sato, Sendai (JP); Takuya Ito, Sendai (JP); Takayuki Shimazaki, Sendai (JP); Junichi Sugawara, Sendai (JP); Masato Senoo, Sendai (JP)

(73) Assignee: Tohoku University (JP)

( * ) Notice: Subject to any disclaimer, the term of this patent is extended or adjusted under 35 U.S.C. 154(b) by 744 days.

(21) Appl. No.: 11/814,230

(22) PCT Filed: Dec. 22, 2005

(86) PCT No.: PCT/JP2005/023601  
§ 371 (c)(1),  
(2), (4) Date: Jul. 18, 2007

(87) PCT Pub. No.: WO2006/080167  
PCT Pub. Date: Aug. 3, 2006

(65) Prior Publication Data  
US 2008/0146953 A1    Jun. 19, 2008

(30) Foreign Application Priority Data  
Jan. 31, 2005   (JP) ................................. 2005-023982

(51) Int. Cl.  
*A61B 5/0444* (2006.01)
(52) U.S. Cl. ....................................................... 600/511
(58) Field of Classification Search .................. 600/511, 600/508, 512, 376, 304  
See application file for complete search history.

(56) References Cited

U.S. PATENT DOCUMENTS

| | | | |
|---|---|---|---|
| 6,658,284 B1 | 12/2003 | Rosen et al. | 600/511 |
| 7,333,850 B2 * | 2/2008 | Marossero et al. | 600/511 |
| 7,474,915 B2 * | 1/2009 | Assaleh et al. | 600/511 |
| 7,509,170 B2 * | 3/2009 | Zhang et al. | 607/28 |

OTHER PUBLICATIONS

Lathauwer, Levin De. et al. "Fetal Electrogram Extraction by Blind Source Subspace Seperation." IEEE Transactions on Biomedical Engineering, vol. 47, No. 5, May 2000.*

(Continued)

*Primary Examiner* — Carl H Layno  
*Assistant Examiner* — Paula J Stice  
(74) *Attorney, Agent, or Firm* — Hayes Soloway P.C.

(57) ABSTRACT

An electrocardiogram signal processing method and device for extracting a fetus electrocardiogram signal included in a biopotential signal detected from an electrode attached to a mother's body is provided. The electrocardiogram signal processing method for extracting an electrocardiogram signal of a fetus (1b) from a biopotential signal containing electrocardiogram signals of the mother's body (1) and a fetus (1b) inputted through an electrode (E) attached to the mother's body (1) during pregnancy, comprises a reference signal generating step 4 of generating a reference signal for separating/extracting a fetus electrocardiogram signal of a specified induction type according to a beat rate signal inputted from a sensor (S) for detecting the beat rate of the fetus (1b) and a fetus electrocardiogram signal extracting step 5 of separating/extracting the fetus electrocardiogram signal of the specified induction type from the biopotential signal inputted through an electrode (E) according to the reference signal generated at reference signal generating step 4 by a reference system independent component analyzing method.

14 Claims, 8 Drawing Sheets

OTHER PUBLICATIONS

Kribeche, Ali. "Seperating fetal Doppler signals in pregnancy using Independent Component Analysis: application to the extraction of fetal heart rate and global movement." IEEE Ultrasonics Symposium vol. 2, 18-21, Sep. 2005.*

Translation of Written Opinion, mailed Feb. 14, 2008.

Sato et al. Extraction of Fetal Electrocardiogram by Blind Source Separation, IEICE Technical Report, vol. 104, No. 429, Nov. 8, 2004, pp. 45-48.

Okamura, Taiji well-being No. Hyoka I. Taiji well-being Shindanho no Hensen to Kongo no Tenbo, Sanka to Fujinka, vol. 71, No. 12, Dec. 1, 2004, pp. 1811-1815.

Rosen Karl G., "Fetal ECG Waveform Analysis in Labour", Ed. SpencerJAD, Castle House Publications, 1989, pp. 184-187.

Teruyuki, Ogawa, "RR interval time-series autoregressive analysis of electrocardiograms of normal fetuses and newborns." The Practice of Time-series Analysis II, Chapter 4, Asakura Publishing Co., 1995, pp. 61-74.

Zarzoso V., "Noninvasive fetal electrocardiogram extraction: Blind separation versus adaptive noise cancellation." IEEE Trans. Biomed. Eng. 48, vol. 1, 2001, pp. 12-18.

Taylor et al., "Non-invasive fetal electrocardiography in singleton and multiple pregnancies." BJOG, 2003, vol. 110, pp. 668-678.

Lathauwer, "Fetal electrocardiogram extraction by source subspace separation." IEEE Trans. Biomed. Eng., 1994, pp. 134-138.

Barros, et al. "Extraction of event-related signals from multichannel bioelectrical measurements." IEEE Trans. Biomed. Eng. vol. 47, No. 5, 2000, pp. 583-588.

* cited by examiner

ELECTROCARDIOGRAM SIGNAL-PROCESSING METHOD AND ELECTROCARDIOGRAM SIGNAL-PROCESSING DEVICE

TECHNICAL FIELD

The present invention relates to an electrocardiogram signal-processing method and an electrocardiogram signal-processing device for detecting the electrocardiogram of fetus in a pregnant mother's body.

BACKGROUND ART

Conventional devices of this type have involved attempts to measure the electrocardiogram signal of a fetus using an abdominal electrocardiogram signal inputted from electrodes positioned on the abdomen of the mother's body. An operation must be performed for separating the feeble signal of the fetus from the abdominal electrocardiogram signal of the mother's body. A variety of methods have been attempted, but a method that is effective regardless of the position and age in weeks of the fetus has not been developed.

In one method currently in actual use, extraction processing is performed using independent component analysis for extracting an electrocardiogram signal primarily on the basis of differences in a probability distribution. However, the electrocardiogram signal extraction magnitude and order cannot be specified, and the method is susceptible to contamination by electromyogram signals and other signals that are close to the probability distribution. Another problem is that the components of a different electrocardiogram of the probability distribution cannot be simultaneously extracted.

The usefulness of fetal electrocardiogram signals is widely recognized, and several extraction algorithms have been proposed. However, few can function on a consistent basis in the various clinical environments; in particular, methods that are effective for the 26th through 36th weeks of pregnancy, in which the SN ratio of the fetal electrocardiogram signal in the abdominal electrocardiogram signal of the mother's body drops precipitously, have not yet been developed.

Fetal electrocardiogram signals inputted from the scalp during delivery have come into primary conventional use due to these problems. This method involves passing directly through the birth canal via the vaginal opening during delivery and attaching a spiral-type unipolar electrocardiogram electrode directly to a portion of the fetus exposed outside the uterus, e.g., to the head or buttocks. Examples of this technique are disclosed in U.S. Pat. No. 6,658,284 to Rosen et al. or in Rosen K G: "Fetal ECG waveform analysis in labour." Fetal monitoring. Physiology and techniques of antenatal and intrapartum assessment. Ed. SpencerJAD. Castle House Publications. pp. 184-187, 1989.

A method for measuring a fetal electrocardiogram signal obtained from an electrode on the scalp of a fetus is described in U.S. Pat. No. 6,658,284 to Rosen at al. and Rosen K G: "Fetal ECG waveform analysis in labour." Fetal monitoring. Physiology and techniques of antenatal and intrapartum assessment. Ed. SpencerJAD. Castle House Publications. pp. 184-187, 1989. However, this method is clearly invasive, and the measurement period is limited to the time of delivery. The invasiveness of the method results in increased risk to the fetus of infection and other problems.

In a similar manner, the intrauterine implanted fetus-monitoring device of Japanese Laid-open Patent Application No. 2004-121733 by Horio et al. is also an invasive method in which a hysteroscope in inserted and a microcapsule is directly attached to the fetus. Invasive surgery on the mother's body is necessary in order to attach the microcapsule to the fetus. Application is therefore limited, and this method has the same problems as the example of U.S. Pat. No. 6,658,284.

Examples of fetal electrocardiogram-signal extraction methods hitherto proposed include a direct method according to Ogawa Teruyuki: "RR interval time-series autoregressive analysis of electrocardiograms of normal fetuses and newborns," The Practice of Time-series Analysis II, Akaike Kouji, Kitagawa Genshirou (editors). Chapter 4, pp. 61-74, Asakura Publishing Co., 1995 by Ogawa et al., in which a template of the electrocardiogram signal of the mother's body is determined and subtracted from the abdominal electrocardiogram signal of the mother's body, and the extraction method of Japanese Translation of PCT International Application No. 2002-538872 by Greenberg et al., which is a mathematically enhanced version of the method of "RR interval time-series autoregressive analysis of electrocardiograms of normal fetuses and newborns" and in which a fetal electrocardiogram signal is extracted using an adaptive-signal processing filter.

In order to obtain the fetal electrocardiogram signal, the aforedescribed methods involve estimating the maternal electrocardiogram and electromyogram signals, which act as noise, and removing these signals from the abdominal electrocardiogram signal of the mother's body, thereby passively extracting the fetal electrocardiogram signal. According to the method disclosed in "RR interval time-series autoregressive analysis of electrocardiograms of normal fetuses and newborns", the noise components are known to unexpectedly change during fetal movement, uterine contractions, activity by the mother's body, or for other reasons. Conversely, when the noise increases or decreases extremely rapidly, when fat components (vernix caseosa) around the fetus begin to increase as in the 26th through 36th weeks of pregnancy, and the fetal electrocardiogram signal is difficult to detect, or at other times when the SN ratio deteriorates, effective extraction is difficult, and precision is known to conspicuously decrease even in comparison to the precision of extraction using mere independent component analysis (BSS).

On the other hand, well-known methods for extracting a fetal electrocardiogram signal using independent component analysis (BSS) include Taylor M J O, at al.: "Non-invasive fetal electrocardiography in singleton and multiple pregnancies" BJOG, 110, 668-78, 2003 by Taylor et al. and "Fetal electrocardiogram extraction by blind source subspace separation" IEEE Trans. Biomed. Eng., 47, 567-572, 2000 by Lathauwer et al. As described earlier, the electrocardiogram signal extraction magnitude and order cannot be specified in these methods, which are also susceptible to contamination by electromyogram signals and other signals that are close to the probability distribution. Additionally, different components of the probability distribution within the electrocardiogram signal cannot be simultaneously extracted. A signal close to the fetal electrocardiogram signal is sought out from among the several independent components in the analysis results and labeled as the fetal electrocardiogram signal. The type of lead type necessary for the analysis of the electrocardiogram signal cannot be designated, meaning these methods are all passive and therefore entail complications in overcoming the practical problems such as described above.

BSS algorithms have also been proposed. In such instances, a reference signal that is similar to the fetal electrocardiogram signal to be extracted is used, and a signal-source waveform that is strongly correlated to the reference signal is estimated. An example of this method is proposed in "Extraction of event-related signals from multi-channel bio-electrical measurements" IEEE Trans. Biomed. Eng. 47, 583-

588, 2000 by Barros at al. In this document, the timing of a periodic function is used as a reference signal, and the periodic function is extracted. However, the number of estimation parameters in this method is enormous. Estimating a 0.5-second phenomenon requires the simultaneous estimation of 100 or more parameters. The algorithm is unstable and the functions that can be estimated are limited. Signal sources that can be used as a reference signal for performing good estimation are also limited. This method is inadequate for actual extraction of a fetal electrocardiogram signal.

Therefore, an effective means for actively and non-invasively retrieving a fetal electrocardiogram signal of a designated lead type from an electrocardiogram electrode positioned on the abdomen of a mother's body has not yet been discovered.

DISCLOSURE OF THE INVENTION

Problems to be Solved by the Invention

In the conventional art as described above, following five problems have arisen; (1) electromyogram noise, 50-Hz high-frequency noise, and other signal sources of similar probability distributions or frequency distributions with fetal electrocardiogram cannot be distinguished. (2) R-waves can be extracted to some extent, but the extraction of P-waves and T-waves is difficult. (3) The lead type necessary for electrocardiogram diagnosis cannot be actively designated. (4) The observation channel on which the fetal electrocardiogram signal will appear cannot be predicted. (5) The precision with which the fetal electrocardiogram signal is extracted is affected by the high-amplitude electrocardiogram signal of the mother's body and deteriorates.

The present invention was devised with attention to such problems, and it is therefore an object of the present invention to provide an electrocardiogram signal-processing method and an electrocardiogram signal-processing device for extracting fetal electrocardiogram signals included in biopotential signals (abdominal electrocardiogram signals) detected from electrodes attached to the mother's body.

Means for Solving the Problems

In order to solve the aforementioned problems, an electrocardiogram signal-processing method according to claim 1 of the present invention is an electrocardiogram signal-processing method for extracting an electrocardiogram signal of a fetus from a biopotential signal containing electrocardiogram signals of the fetus and of a mother's body inputted via electrodes attached to the pregnant mother's body, characterized in comprising:

a reference-signal generating step for generating a reference signal, on the basis of a heartbeat-period signal inputted from a detector for detecting a heartbeat period of the fetus, in order to separate and extract a fetal electrocardiogram signal of a designated lead type; and a fetal electrocardiogram-signal extracting step for separating and extracting the fetal electrocardiogram signal of the designated lead type from the biopotential signal, which was inputted from the electrodes, by using blind source separation with reference signals on the basis of the reference signal generated in the reference-signal generating step.

According to this characteristic, a biopotential signal can be non-invasively detected from electrodes attached to the mother's body. A reference signal based on the fetal heartbeat period detected by the detector is used, and a fetal electrocardiogram signal is separated and extracted from the biopotential signal using independent component analysis (ICA) with references, whereby a fetal electrocardiogram signal of the designated lead type can be actively extracted.

An electrocardiogram signal-processing method according to claim 2 of the present invention is the electrocardiogram signal-processing method according to claim 1, characterized in that the heartbeat-period signal is an ultrasound signal inputted from an ultrasound sensor that can be attached to the mother's body.

According to this characteristic, an ultrasound signal of the heart of the fetus can be unambiguously recovered at all weeks of pregnancy. The SN ratio of the ultrasound signal is also good, and therefore the reference signal generated on the basis of this ultrasound signal is used in the independent component analysis of the fetal electrocardiogram-signal extracting step, thereby allowing the fetal electrocardiogram signal to be extracted from the biopotential signal at a high probability.

An electrocardiogram signal-processing method according to claim 3 of the present invention is the electrocardiogram signal-processing method according to claim 1 or 2, characterized in comprising:

a maternal electrocardiogram signal removing step for removing, from the biopotential signal inputted from the electrodes, a primary component of an electrocardiogram of the mother's body, which is based on the electrocardiogram signal of the mother's body inputted via maternal electrodes attached primarily to a chest part of the mother's body.

According to this characteristic, the maternal electrocardiogram signal is removed from the biopotential signal in advance, whereby the fetal electrocardiogram signal is more readily extracted by the independent component analysis performed in the fetal electrocardiogram-signal extracting step.

An electrocardiogram signal-processing method according to claim 4 of the present invention is the electrocardiogram signal-processing method according to claim 3, characterized in comprising:

an averaged biopotential-signal generating step for averaging a plurality of biopotential signals inputted from the electrodes that are attached so that the biopotential signals obtained at a plurality of different locations on the mother's body have spatially independent vector components, and for generating an averaged biopotential signal; and an averaged maternal electrocardiogram-signal generating step for averaging a plurality of electrocardiogram signals of the mother's body inputted from the maternal electrodes, which are attached so that the biopotential signals obtained at a plurality of different locations primarily on the chest part of the mother's body have spatially independent vector components, and for generating an averaged maternal electrocardiogram signal, wherein In the maternal electrocardiogram signal removing step, the primary component of the electrocardiogram of the mother's body, which is based on the averaged maternal electrocardiogram signal generated in the averaged maternal electrocardiogram-signal generating step, is removed from the averaged biopotential signal generated in the averaged biopotential-signal generating step.

According to this characteristic, the primary components of the electrocardiogram of the mother's body, which are based on the averaged maternal electrocardiogram signal generated in the averaged maternal electrocardiogram-signal generating step, are removed from the averaged biopotential signal generated in the averaged biopotential-signal generating step, allowing the removal of the primary components of the electrocardiogram of the mother's body, which may become highly correlated with the reference signal used in the independent component analysis of the fetal electrocardiogram-signal extracting step, and allowing the fetal electrocardiogram signal to be readily extracted from the biopotential signal in the fetal electrocardiogram-signal extracting step.

An electrocardiogram signal-processing method according to claim 5 of the present invention is the electrocardiogram signal-processing method according to claim 3 or 4, characterized in that in the maternal electrocardiogram signal removing step, a transformation vector is created on the basis of weighting using the least-squares method from the averaged maternal electrocardiogram signal generated in the averaged maternal electrocardiogram-signal generating step and/or an averaged maternal electrocardiogram signal generated by averaging a plurality of temporally repeating units included in the electrocardiogram signal of the mother's body inputted from one maternal electrode; and the primary component of the electrocardiogram of the mother's body is removed on the basis of the maternal electrocardiogram signal estimated using the created transformation vector.

According to this characteristic, a transformation vector is created by weighting using the least-squares method from the averaged maternal electrocardiogram signal generated in the averaged maternal electrocardiogram-signal generating step and/or an averaged maternal electrocardiogram signal generated by averaging a plurality of temporally repeating units included in the electrocardiogram signal of the mother's body inputted from one maternal electrode. By using this transformation vector, the primary components of the electrocardiogram of the mother's body can be rapidly removed from the averaged maternal electrocardiogram signal, the processing load during the maternal electrocardiogram signal removing step is reduced, and processing can be performed online in real-time.

An electrocardiogram signal-processing method according to claim 6 of the present invention is the electrocardiogram signal-processing method according to any of claims 1 through 5, characterized in comprising:

a re-montaging step for reorganizing bipolar terminals of the electrodes in an optimal combination on the basis of inputted information concerning a position of the fetus in order to perform at least the fetal electrocardiogram-signal extracting step.

According to this characteristic, the bipolar terminals of the electrodes are reorganized in an optimal combination on the basis of inputted information concerning the position of the fetus, whereby the fetal electrocardiogram signal included in the biopotential signal detected by the electrodes can be increased, and a good fetal electrocardiogram signal can be obtained in the fetal electrocardiogram-signal extracting step.

An electrocardiogram signal-processing method according to claim 7 of the present invention is the electrocardiogram signal-processing method according to any of claims 1 through 6, characterized in that in the reference-signal generating step, a value of the fetal heartbeat period is specified on the basis of the heartbeat-period signal; a template signal that conforms to the designated lead type is selected from a plurality of template signals; and the reference signal is generated on the basis of the selected template signal so that a period value will be identical to the specified value of the fetal heartbeat period.

According to this characteristic, a plurality of template signals are prepared in advance, whereby the processing load is reduced when the reference signal is generated during the reference-signal generating step, and the reference signal can be rapidly generated. A template signal that conforms to the designated lead type is selected from a plurality of template signals, and the reference signal is generated on the basis of this template signal so that a period value will be identical to the value of the fetal heartbeat period, thereby allowing the fetal electrocardiogram signal to be extracted from the biopotential signal at a high probability using independent component analysis in the fetal electrocardiogram-signal extracting step in which the reference signal is used.

An electrocardiogram signal-processing device according to claim 8 of the present invention is an electrocardiogram signal-processing device for extracting an electrocardiogram signal of a fetus from a biopotential signal containing electrocardiogram signals of the fetus and of a mother's body inputted via electrodes attached to the pregnant mother's body, characterized in comprising:

a heartbeat-period generating signal inputting section for inputting a heartbeat-period generating signal of the fetus; reference-signal generating means for generating a reference signal on the basis of the heartbeat-period signal inputted from the heartbeat-period generating signal inputting section, in order to separate and extract a fetal electrocardiogram signal of a designated lead type; and fetal electrocardiogram-signal extracting means for separating and extracting the fetal electrocardiogram signal of the designated lead type from the biopotential signal, which was inputted from the electrodes, by using ICA with references on the basis of the reference signal generated by the reference-signal generating means.

According to this characteristic, a biopotential signal can be non-invasively detected from electrodes attached to the mother's body. A reference signal based on the fetal heartbeat period detected by the heartbeat-period generating signal inputting section is used, and a fetal electrocardiogram signal is separated and extracted from the biopotential signal using independent component analysis, whereby a fetal electrocardiogram signal of the designated lead type can be actively extracted.

An electrocardiogram signal-processing device according to claim 9 of the present invention is the electrocardiogram signal-processing device according to claim 8, characterized in that the heartbeat-period generating signal inputted to the heartbeat-period generating signal inputting section is an ultrasound signal inputted from an ultrasound sensor that can be attached to the mother's body.

According to this characteristic, an ultrasound signal of the heart of the fetus can be unambiguously recovered at all weeks of pregnancy. The SN ratio of the ultrasound signal is also good, and therefore the reference signal generated on the basis of this ultrasound signal is used in the independent component analysis of the fetal electrocardiogram-signal extracting means, thereby allowing the fetal electrocardiogram signal to be extracted from the biopotential signal at a high probability.

An electrocardiogram signal-processing device according to claim 10 of the present invention is the electrocardiogram signal-processing device according to claim 8 or 9, characterized in comprising:

maternal electrocardiogram signal removing means for removing, from the biopotential signal inputted from the electrodes, a primary component of an electrocardiogram of the mother's body, which is based on the electrocardiogram signal of the mother's body inputted via maternal electrodes attached primarily to a chest part of the mother's body.

According to this characteristic, the maternal electrocardiogram signal is removed from the biopotential signal in advance, whereby the fetal electrocardiogram signal is more readily extracted by the ICA with references performed by the fetal electrocardiogram-signal extracting means.

An electrocardiogram signal-processing device according to claim 11 of the present invention is the electrocardiogram signal-processing device according to claim 10, characterized in comprising:

averaged biopotential-signal generating means for averaging a plurality of biopotential signals inputted from the electrodes, which are attached so that the biopotential signals obtained at a plurality of different locations on the mother's body have spatially independent vector components, and for generating an averaged biopotential signal; and averaged maternal electrocardiogram-signal generating means for averaging a plurality of electrocardiogram signals of the mother's body inputted from the maternal electrodes, which are attached so that the biopotential signals obtained at a plurality of different locations primarily on the chest part of the mother's body have spatially independent vector components, and for generating an averaged maternal electrocardiogram signal, wherein In the maternal electrocardiogram signal removing means, the primary component of the electrocardiogram of the mother's body, which is based on the averaged maternal electrocardiogram signal generated by the averaged maternal electrocardiogram-signal generating means, is removed from the averaged biopotential signal generated by the averaged biopotential-signal generating means.

According to this characteristic, the primary components of the electrocardiogram of the mother's body, which are based on the averaged maternal electrocardiogram signal generated by the averaged maternal electrocardiogram-signal generating means, are removed from the averaged biopotential signal generated by the averaged biopotential-signal generating means, allowing the removal of the primary components of the electrocardiogram of the mother's body, which may become highly correlated with the reference signal used in the independent component analysis of the fetal electrocardiogram-signal extracting means, and allowing the fetal electrocardiogram signal to be readily extracted from the biopotential signal by the fetal electrocardiogram-signal extracting means.

An electrocardiogram signal-processing device according to claim 12 of the present invention is the electrocardiogram signal-processing device according to claim 10 or 11, characterized in that in the maternal electrocardiogram signal removing means, a transformation vector is created on the basis of weighting using the least-squares method from the averaged maternal electrocardiogram signal generated by the averaged maternal electrocardiogram-signal generating means and/or an averaged maternal electrocardiogram signal generated by averaging a plurality of temporally repeating units included in the electrocardiogram signal of the mother's body inputted from one maternal electrode; and the primary component of the electrocardiogram of the mother's body is removed on the basis of the maternal electrocardiogram signal estimated using the created transformation vector.

According to this characteristic, a transformation vector is created by weighting using the least-squares method from the averaged maternal electrocardiogram signal generated by the averaged maternal electrocardiogram-signal generating means and/or an averaged maternal electrocardiogram signal generated by averaging a plurality of temporally repeating units included in the electrocardiogram signal of the mother's body inputted from one maternal electrode. By using this transformation vector, the primary components of the electrocardiogram of the mother's body can be rapidly removed from the averaged maternal electrocardiogram signal, the processing load in the maternal electrocardiogram signal removing means is reduced, and processing can be performed online in real-time.

An electrocardiogram signal-processing device according to claim 13 of the present invention is the electrocardiogram signal-processing device according to any of claims 8 through 12, characterized in comprising:

re-montaging means for reorganizing bipolar terminals of the electrodes in an optimal combination on the basis of inputted information concerning a position of the fetus in order to at least separate and extract the fetal electrocardiogram signal using the fetal electrocardiogram-signal extracting means.

According to this characteristic, the bipolar terminals of the electrodes are reorganized in an optimal combination on the basis of inputted information concerning the position of the fetus, whereby the fetal electrocardiogram signal included in the biopotential signal detected by the electrodes can be increased, and a good fetal electrocardiogram signal can be obtained by the fetal electrocardiogram-signal extracting means.

An electrocardiogram signal-processing device according to claim 14 of the present invention is the electrocardiogram signal-processing device according to any of claims 8 through 13, characterized in that in the reference-signal generating means, a value of the fetal heartbeat period is specified on the basis of the heartbeat-period signal; a template signal that conforms to the designated lead type is selected from a plurality of previously stored template signals; and the reference signal is generated on the basis of the selected template signal so that a period value will be identical to the specified value of the fetal heartbeat period.

According to this characteristic, a plurality of template signals are stored in advance in the reference-signal generating means, whereby the processing load is reduced when the reference signal is generated in the reference-signal generating means, and the reference signal can be rapidly generated. A template signal that conforms to the designated lead type is selected from a plurality of template signals, and the reference signal is generated on the basis of this template signal so that a period value will be identical to the value of the fetal heartbeat period, thereby allowing the fetal electrocardiogram signal to be extracted from the biopotential signal at a high probability using independent component analysis in the fetal electrocardiogram-signal extracting means in which the reference signal is used.

KEY

A Electrocardiogram signal-processing device
1 Mother's body
1b Fetus
3 Maternal-signal removing section (maternal electrocardiogram signal removing means)
4 Reference-signal generating section (reference-signal generating means)
5 Main computing section (fetal electrocardiogram-signal extracting means)
11 Re-montaging section (re-montaging means)
14 Maternal-cardiogram estimating section (averaged maternal electrocardiogram-signal generating means)
15 Estimated maternal-cardiogram removing section (averaged biopotential-signal generating means)
17 Heartbeat-period generating signal inputting section
E Electrode
E' Maternal electrode
S Ultrasound sensor (detector)

BEST MODE FOR CARRYING OUT THE INVENTION

An example of the present invention will be described below.

Example

Figure 1:
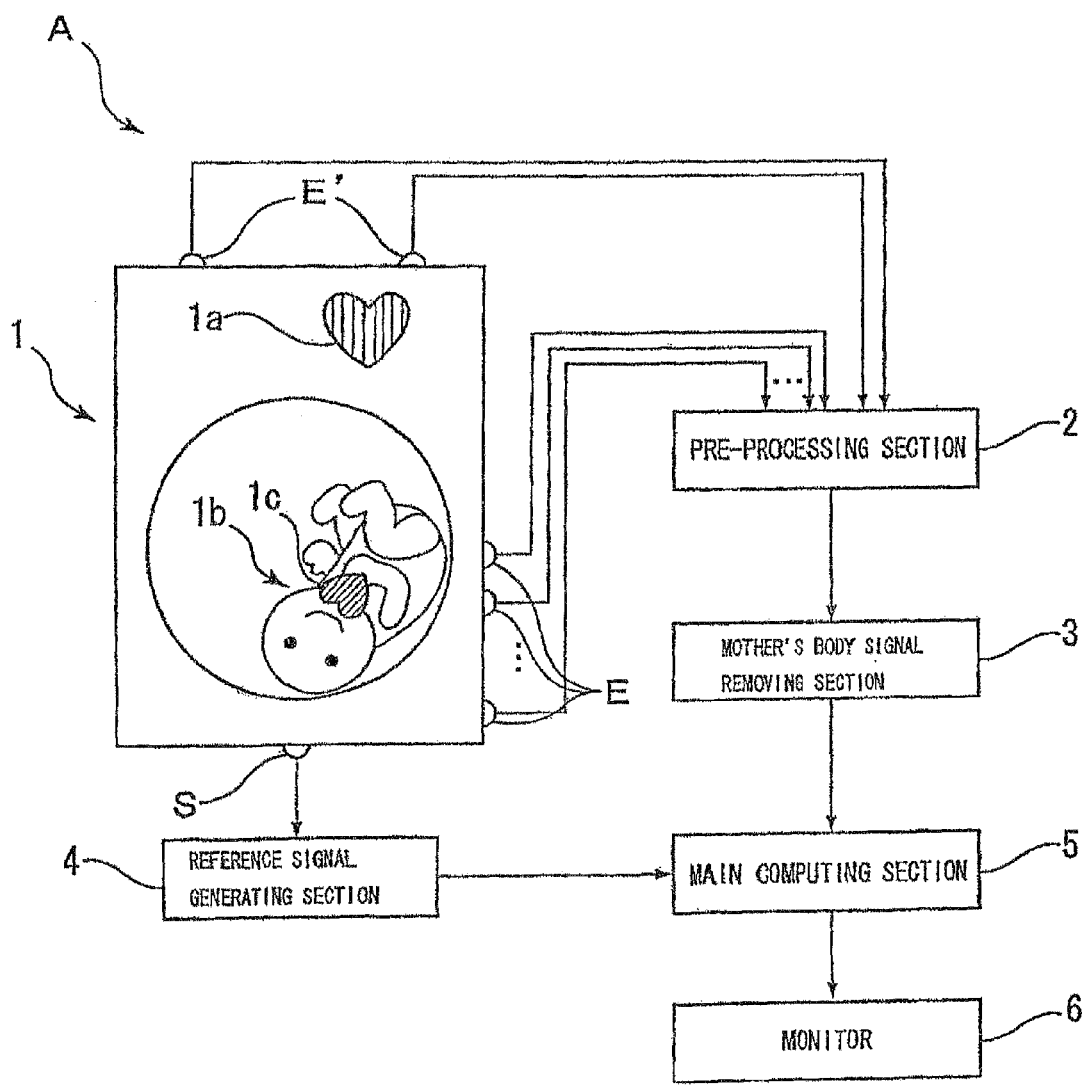
FIG. 1 is a diagram that shows an overall representation of the electrocardiogram signal-processing device.
Figure 2:
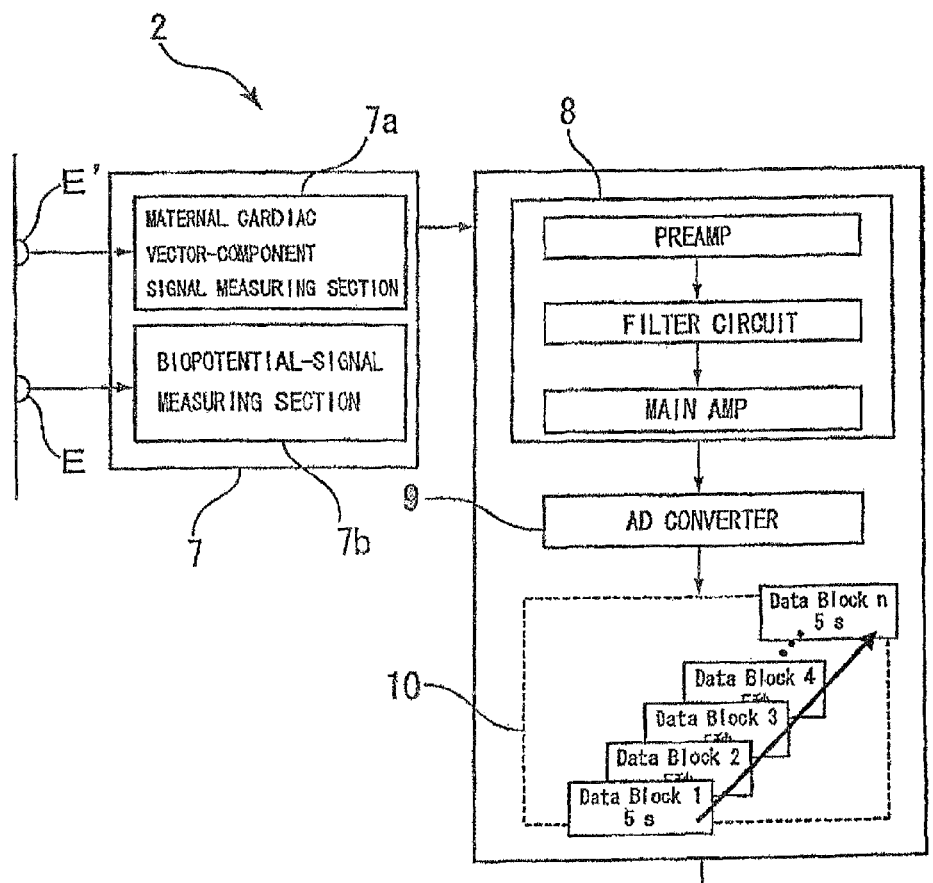
FIG. 2 is a block diagram of the pre-processing section.

Referring to FIGS. 1 and 2 present initial description of the present invention and show an overall representation of an electrocardiogram signal-processing device A of the example of the present invention. The symbol "1" in FIG. 1 designates a pregnant mother's body as a detection object. A plurality of electrodes E are attached to the skin on the abdomen of the mother's body 1. A biopotential signal is detected by the electrodes E positioned on the abdomen. This biopotential signal is a composite biosignal resulting from the combination of the maternal electrocardiogram signal produced by the maternal heart 1a of the mother's body 1, uterine-muscle electromyogram signals, maternal electromyogram signals, and a variety of other signals. Included in this biopotential signal (composite biosignal) is a fetal electrocardiogram signal produced by the fetal heart 1c of a fetus 1b within the uterus of the mother's body 1.

A plurality of maternal electrodes E' are also attached primarily to the skin of the chest of the mother's body 1, as shown in FIG. 1. Signals of maternal cardiac vector components that arrive directly through the surrounding space and are components of the maternal electrocardiogram signal devoid of the components of the fetal electrocardiogram-signal are detected by these maternal electrodes E'. An ultrasound sensor S that acts as a detector in the present example is also attached to the skin of the abdomen of the mother's body 1. The heartbeat produced by the fetal heart 1c becomes an ultrasound signal and is detected by the ultrasound sensor S. The heartbeat period of the fetal heart 1c contained in this ultrasound signal is used as a heartbeat-period signal (reference-source signal) when generating a reference signal, which is described hereinafter.

The symbol "2" in FIG. 1 designates a pre-processing section for converting the biopotential signal, which is detected by the electrodes E attached to the mother's body 1, into a digital signal for analysis. The pre-processing section 2 divides data into intervals for measurement of the biopotential signal, signal amplification, AD conversion, and online processing; augments the fetal electrocardiogram signal included in the biopotential signal; and performs the re-montaging step for reducing shared noise.

The symbol "3" in FIG. 1 designates a maternal electrocardiogram signal removing section that acts as the maternal electrocardiogram signal removing means in the present example in order to remove the primary components of the maternal electrocardiogram signal from the biopotential signal input from the electrodes E of the mother's body 1. The maternal electrocardiogram signal removing step is performed in the maternal-signal removing section 3. In this step, the maternal electrocardiogram signal, which has the potential to become highly correlated with the hereinafter described reference signal, is removed from the biopotential signal beforehand. By removing the maternal electrocardiogram signal from the biopotential signal beforehand, the fetal electrocardiogram signal can be more readily extracted using referential independent component analysis, which is described later.

The symbol "4" in FIG. 1 designates a reference-signal generating section that acts as the reference-signal generating means in the present example in order to generate a reference signal for separating and extracting a fetal electrocardiogram signal of the designated lead type from the biopotential signal. The reference-signal generating step is performed in the reference-signal generating section 4. In this step, a reference signal is generated in order to separate and extract a fetal electrocardiogram signal of the designated induction type. The reference signal is generated on the basis of the heartbeat-period signal of the fetal heart 1c detected by at least one or more ultrasound sensors S (devices for measuring ultrasound signals) or other heartbeat-period signal inputting sections 17 positioned outside the mother's body 1.

This reference signal is used for extracting a fetal electrocardiogram signal of the designated lead type in the fetal electrocardiogram-signal extracting step, which is described hereinafter, and is therefore presupposed to be highly correlated with the fetal electrocardiogram signal of the designated lead type that serves at the object of extraction. The reference-signal generating step is performed in the reference-signal generating section 4. In this step, a value of the fetal heartbeat period specified from the heartbeat-period signal of the fetal heart 1c or other signals is used as a timing function, a template signal corresponding to the target lead type of the fetal electrocardiogram signal is selected from among a plurality of previously stored template signals, and the selected template signal is linked to the timing-function signal, whereby a reference signal is generated having the same period value as the fetal heartbeat.

The symbol "5" in FIG. 1 designates a main computing section that acts as the fetal electrocardiogram-signal extracting means in the present example for performing the fetal electrocardiogram-signal extracting step, in which a fetal electrocardiogram signal of the designated lead type is actively extracted from the biopotential signal using the reference signal generated in the reference-signal generating step. Referential independent component analysis is used in the main computing section 5 on the basis of the reference signal generated in the reference-signal generating step, whereby the fetal electrocardiogram signal is extracted from the biopotential signal. The electrocardiogram waveform of the fetal heart 1c generated on the basis of the extracted fetal electrocardiogram signal is displayed on a monitor 6.

The pre-processing section 2 will next be described in detail using FIG. 2, which is a block diagram of the pre-processing section 2. The pre-processing section 2 comprises a measuring section 7 to which the biopotential signal is input from the electrodes E attached to the mother's body 1; a signal-amplifying section 8 for amplifying the biopotential signal obtained by the measuring section 7; an AD converting section 9 for converting the input analog signal into a digital signal; a data buffer-memory section 10 for storing data for each block capable of online computation and for outputting to the next step; and a re-montaging section 11 that acts as the re-montaging means in the present example for performing the re-montaging step.

As shown in FIG. 2, the measuring section 7 contains spatially independent maternal cardiac vector-component signals that act as the measured biopotential signal. The measuring section comprises a maternal cardiac vector-component signal measuring section 7a for measuring the maternal electrocardiogram signals that are input from at least two or more maternal electrodes E' and that do not include the fetal electrocardiogram signal; and a biopotential-signal measuring section 7b for measuring the biopotential signal, which includes the fetal electrocardiogram signal and is input from at least two or more electrodes E.

As an example of the measuring section 7 of FIG. 2, the maternal electrocardiogram signal induced by the maternal electrodes E' positioned primarily on the chest of the mother's body 1 contains two or more spatially independent vector components that have a cardiac-vector structure and does not include the fetal electrocardiogram signal. These two or more groups of maternal electrocardiogram signals are used as maternal cardiac-vector component signals and employed when removing the maternal electrocardiogram signal from the biopotential signal that includes the fetal electrocardiogram signal. The electrodes E and the maternal electrodes E' that are used for measurement are preferably placed on the chest and abdomen of the mother's body 1, but this case is not given by way of limitation. Electrodes may also be placed on the lateral abdominal parts, back, hips or other locations on the mother's body 1 in order to optimize referential independent component analysis.

The pre-processing section 2 is also provided with the signal-amplifying section 8, which comprises a preamp, a filter circuit, and a main amp for amplifying the resulting biopotential signal; the AD converting section 9 for AD converting the amplified signal; and the data buffer-memory section 10 for storing data for each block capable of online computation and for outputting to the next step. The time interval of the stored data blocks is of a length that allows calculations to be performed online. If the length allows convergence using iterative estimation, which is described hereinafter, a special time interval is not necessary, but a time interval of 5 seconds is used in the present example. Data are stored consecutively in block units for each period of n seconds (n is preferably 5 seconds or less) in the data buffer-memory section 10, and the blocks are output in the order of storage.

The re-montaging step is performed in the re-montaging section 11 shown in FIG. 2. In this step, the bipolar terminals of the electrodes E and the maternal electrodes E' attached to the mother's body 1 are reorganized into an optimal configuration on the basis of input information concerning the position of the fetus 1b in order to perform data analysis in the maternal electrocardiogram signal removing step and the fetal electrocardiogram-signal extracting step, and the biopotential signal is output to the maternal-signal removing section 3. "Optimal" in this instance refers to a state wherein a maximized fetal electrocardiogram signal is included, the maternal electrocardiogram signal and other noise are excluded using a method for minimizing common noise, and the SN ratio (signal-to-noise ratio) relative to other noise is approximately 1 or less. This function is useful for optimization and clarification of the signal when a good fetal electrocardiogram signal is not obtained, but this function is not necessarily essential in general cases in which a clear signal is obtained.

The maternal-signal removing section 3 will be described in detail next using FIG. 3, which is a block diagram of the maternal-signal removing section 3. The maternal-signal removing section 3 comprises a maternal cardiogram-estimating section 14 that acts as the averaged maternal electrocardiogram-signal generating means in the present example for performing the averaged maternal electrocardiogram-signal generating step and for estimating the maternal electrocardiogram signal included in the biopotential signal. In the averaged maternal electrocardiogram-signal generating step, a plurality of maternal cardiac-vector component signals (maternal electrocardiogram signals) are averaged, and an averaged maternal electrocardiogram signal is generated. The maternal cardiac-vector component signals are detected by the maternal electrodes E' attached to a plurality of different locations primarily on the chest of the mother's body 1 and are input from the pre-processing section 2. The maternal-signal removing section also comprises an estimated maternal-cardiogram removing section 15 that acts as the averaged biopotential-signal generating means in the present example for performing the averaged biopotential-signal generating step, removing the maternal electrocardiogram signal from the biopotential signal, and generating a new biopotential signal (averaged biopotential signal). In the averaged biopotential-signal generating step, a plurality of biopotential signals are averaged. These biopotential signals are detected by the electrodes E attached to a plurality of different locations on the mother's body 1 and input from the pre-processing section 2.

Figure 3:
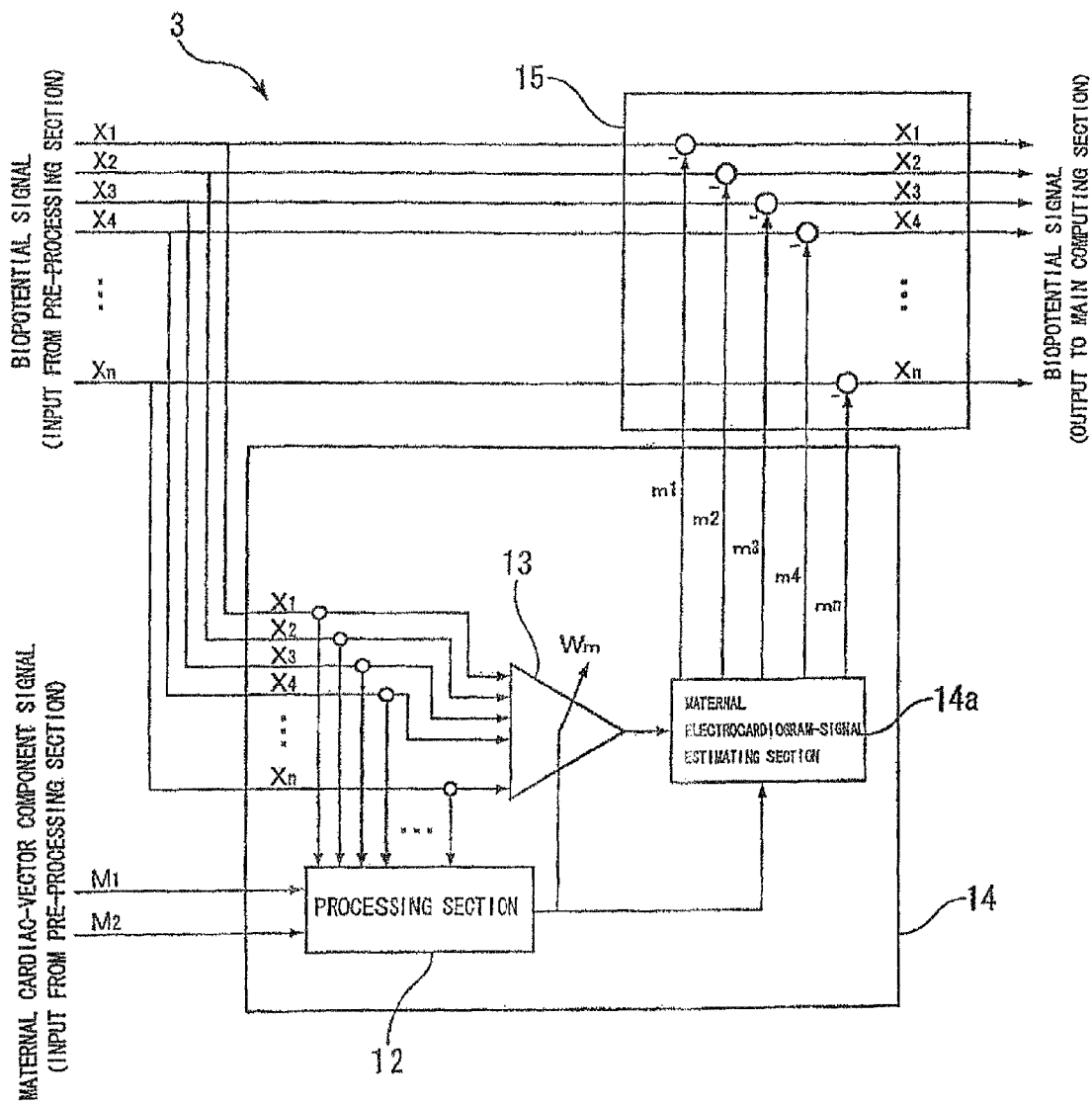
FIG. 3 is a block diagram of the maternal-signal removing section.

The maternal electrocardiogram signal included in the biopotential signal is estimated in the maternal cardiogram-estimating section 14 shown in FIG. 3 using the maternal cardiac-vector component signals. This estimation is implemented by using the average value of at least two or more maternal cardiac-vector component signals, using the least-squares method to perform weighting, and creating a transformation vector for estimating the m number of maternal electrocardiogram signals in the biopotential signals (adequate results will be obtained by estimating merely the R-wave of the mother's body 1, but the R-wave is preferably introduced in 5 or more estimation intervals). An example in which the average value is used and weighting is performed using the least-squares method is given below.

The transformation matrix $Wm=(Wmi)^T$ (where $Wmi=(ai, bi)^T$, and $i=1$ through n) is calculated as the least-squares average value of the difference between the independent maternal cardiac-vector component signals M1, M2 and the maternal R-wave portions of the biopotential signal $x=(xi)$ (where $i=1$ through n); i.e., as the Wmi satisfying the smallest value of $E[(xi-(aiM1+biM2))^T]$ (where $E(*)$ is the time average) (Processing section 12, and Transform vector estimating section 13). This calculation is performed D times (where, e.g., D=5) for different R-waves, and Wm is calculated from the average. The maternal electrocardiogram signals (m1 through mn) of the detection values are estimated using the transformation Wm and aiM1+biM2 (maternal electrocardiogram-signal estimating section 14a).

The maternal electrocardiogram signals (m1 through mn) of the detection values estimated using the transformation Wm in the maternal cardiogram-estimating section 14 are removed from the biopotential signal (estimated maternal-cardiogram removing section 15). This maternal electrocardiogram signal removing step involves removing to a certain extent the components that may become highly correlated with the reference signal in the fetal electrocardiogram-signal extracting step, which is described hereinafter, and is performed in order to reduce this correlation. Complete removal is preferable but is not necessarily essential.

The transformation vector that is created to estimate the maternal electrocardiogram signal may be created by weighting using the least-squares method from the averaged maternal electrocardiogram signal generated in the averaged maternal electrocardiogram-signal generating step. Alternatively, a plurality of temporally repeating units included in the maternal electrocardiogram signal input from one maternal electrode E' may be averaged to generate an averaged maternal electrocardiogram signal, and the transformation vector may be created from this averaged maternal electrocardiogram signal by weighting using the least-squares method. The processing load during the maternal electrocardiogram signal removing step is thereby reduced, the primary components of the maternal electrocardiogram signal can be rapidly removed, and processing can be performed online in real time.

In the present example, the calculation is performed D times (where, e.g., D=5) for different R-waves, which act as the plurality of temporally repeating units, the transformation Wm is calculated from the average, and the maternal electrocardiogram signal is estimated, but the present invention is not limited to this case. The maternal electrocardiogram signal included in the biopotential signal may also be estimated using the average value determined from averaging the plurality of maternal electrocardiogram signals detected by the electrodes E attached to the mother's body 1 without performing these calculations, i.e., without averaging a plurality of temporally repeating units and calculating the averaged maternal electrocardiogram signal.

The reference-signal generating section 4 will be described in detail next using FIG. 4, which is a block diagram of the reference-signal generating section 4. The reference-signal generating section 4 comprises a template-signal storing section 22 for storing a plurality of previously generated template signals; a heartbeat-period generating signal inputting section 17 for inputting the heartbeat-period generating signals obtained from at least one or more ultrasound sensors S or like attached to the abdomen of the mother's body 1; a filter 18 for filtering the input heartbeat-period signals; a timing-function calculating section 19 for determining an approximate value for the fetal heartbeat period (the timing function) from the input heartbeat-period signals; a timing-function signal generating section 20 for generating a timing-function signal on the basis of the value of the fetal heartbeat period; a checking section 21b for detecting abnormalities in the timing-function signal generated by the timing-function signal generating section 20; a feedback section 21a for feeding back the timing-function signal when abnormalities are detected by the checking section 21b; and a reference-signal generating section 23 for linking the template signal selected by the template-signal storing section 22 to the timing-function signal and creating a reference signal.

Figure 4:
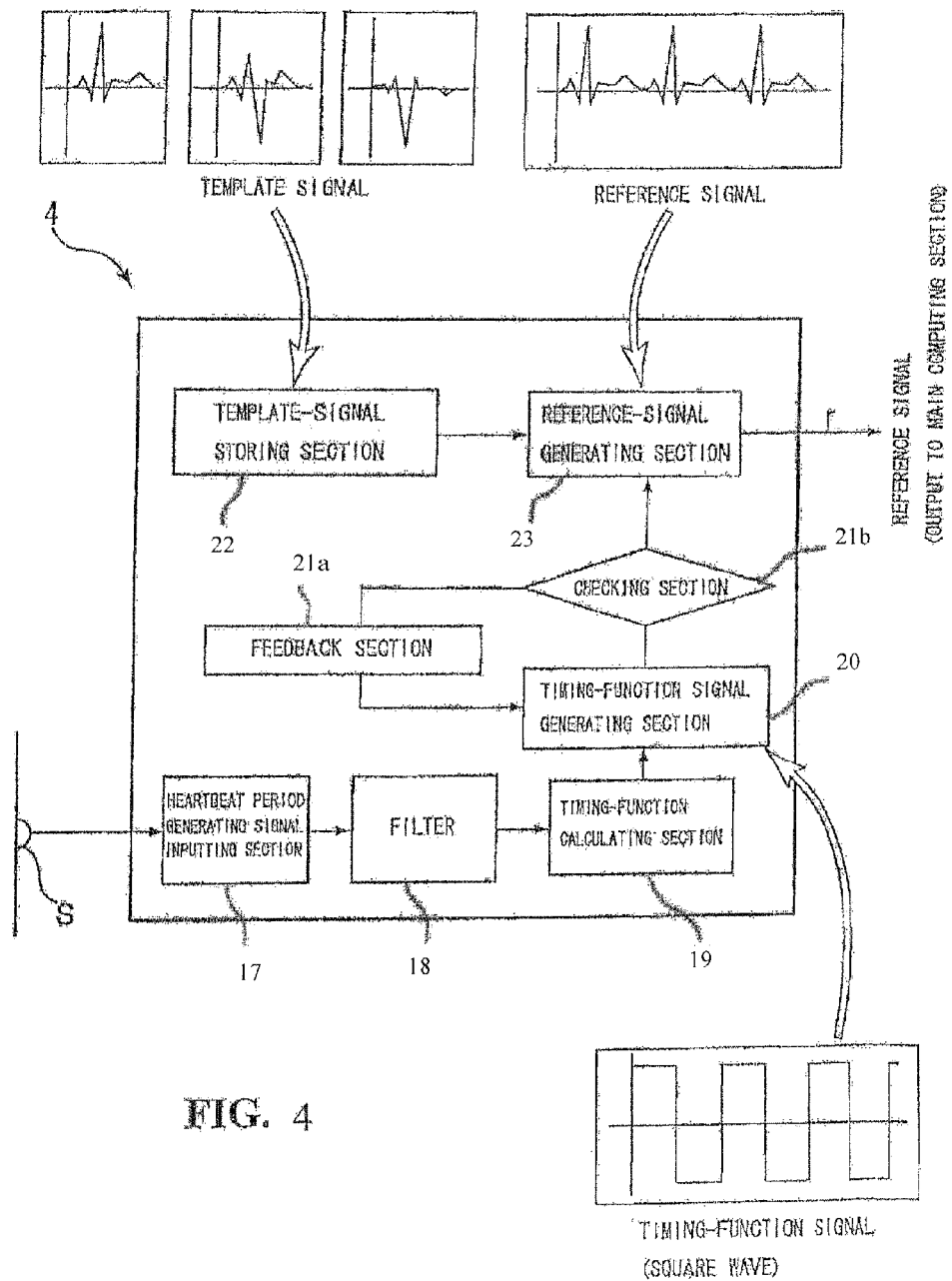
FIG. 4 is a block diagram of the reference-signal generating section.

As shown in FIG. 4, the heartbeat-period signal obtained from the fetal heart 1c (reference-signal source) using the ultrasound sensor S is input to the heartbeat-period generating signal inputting section 17, filtered by the filter 18, and then measured by the timing-function calculating section 19. The value for the fetal heartbeat period is specified by the timing-function calculating section 19, and a timing function having the same period value as the fetal heartbeat is specified. A timing-function signal (square wave) is then generated by the timing-function signal generating section 20 on the basis of this timing function. The heartbeat-period generating signal is most preferably an ultrasound signal that is detected by the ultrasound sensor S.

Time resolution is high if the fetal electrocardiogram signal can be extracted as generally described, but the signal will be faint at $\frac{1}{5}$ to $\frac{1}{10}$ of the maternal electrocardiogram signal, and the SN ratio for extracting fetal components will be low at 1 or less. However, the ultrasound signal of the fetal heart 1c can be unambiguously retrieved at all weeks of pregnancy. The SN ratio is good at 3 to 5, but the resulting signal will be characterized by poor time resolution. The signal characteristics are different in both cases, and by using the fetal cardiac ultrasound signal to extract the heartbeat-period generating signal of the fetal heart 1c, the two cases will mutually complement one another. The reference series, which has a high SN ratio, is therefore used as a key in the main computing section 5, which is described hereinafter, allowing a high probability of extracting the desired fetal electrocardiogram signal with high time resolution.

The timing-function signal will next be described in more detail. The band-pass filter 18 is used to extract fetal cardiac Doppler components in the band from 100 Hz to 600 Hz when the heartbeat-period signal is a fetal cardiac ultrasound signal. Calculation is performed in the timing-function calculating section 19 using autocorrelation. Specifically, an envelope is taken at 14 Hz on the Doppler signal that has passed through the filter 18, the time interval (value of the fetal heartbeat period) from each 1.5-second autocorrelation to the next heartbeat is calculated, and a timing-function signal (square wave), which changes to square form in time with the generation of heartbeats, is generated on the basis of this value. In the feedback section 21a shown in FIG. 4, noise and the like may occur in the ultrasound signal detected by the ultrasound sensor S due to, e.g., sudden movements of the fetus 1b, but the timing-function signal generated at such times using the ultrasound signal that is contaminated with noise will be a square wave having a shape different from previous timing-function signals. When the checking section 21b detects this abnormality, the feedback section 21a replaces the timing-function signal with the average value of the values for the fetal heartbeat period detected up to that point, whereby a timing-function signal is once again generated and output.

A plurality of template signals (single-period waveforms) that approximate fetal electrocardiogram signals of designated lead types are stored beforehand in the template-signal storing section 22 of FIG. 4. The template signal that conforms to the designated lead type is selected from among these template signals and output to the reference-signal generating section 23.

The template signal selected by the template-signal storing section 22 is harmonized with the timing of the square wave of the timing-function signal and linked on the time axis in the reference-signal generating section 23, and a reference signal r is generated. The reference signal r is generated on the basis of the heartbeat-period signal so as to have the strongest correlation with the fetal electrocardiogram signal of the designated lead type that is the object of extraction within the biopotential signal. This reference signal is used in the ICA with references, which is described hereinafter.

Figure 5:
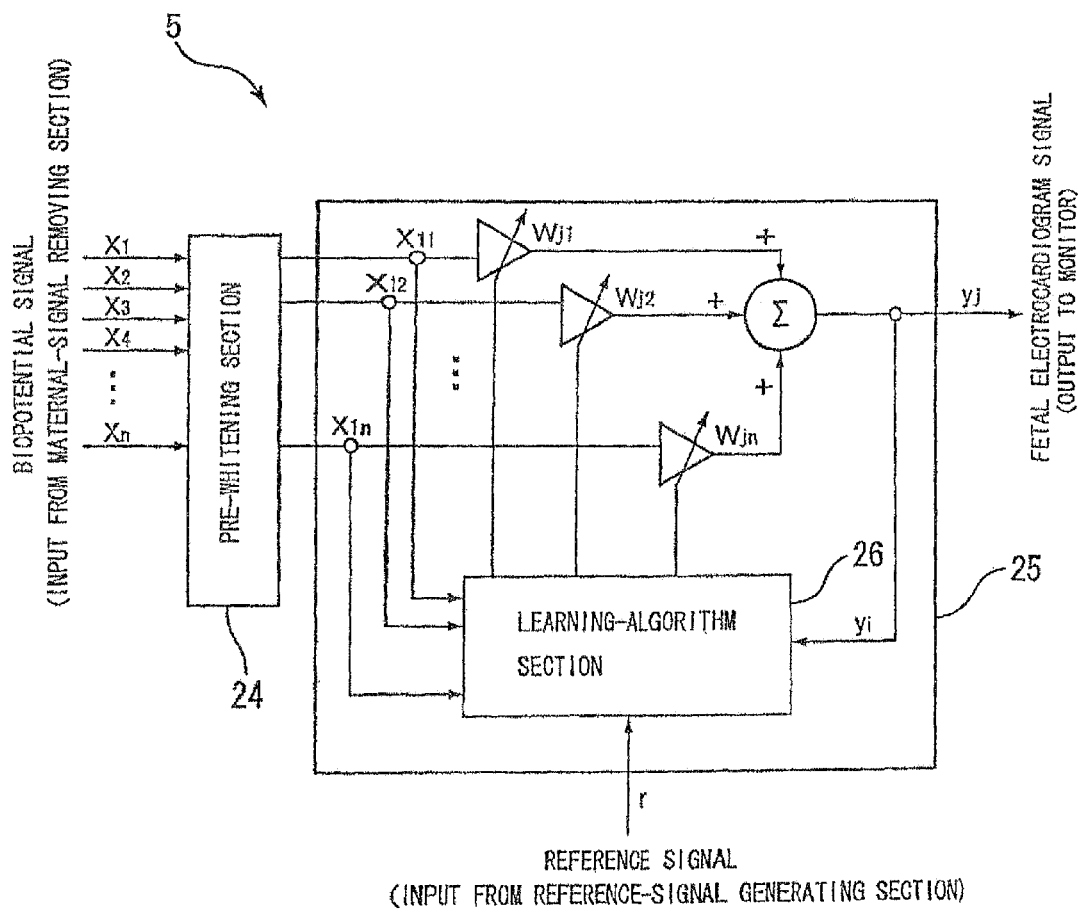
FIG. 5 is a block diagram of the main computing section.

The main computing section 5 will be described in detail next using FIG. 5, which is a block diagram of the main computing section 5. Referential independent component analysis is used in the main computing section 5, and the fetal electrocardiogram-signal extracting step is performed. In this step, the reference signal is used as a key, and the fetal electrocardiogram signal is extracted from the biopotential signal. The main computing section 5 comprises a pre-whitening section 24 for mutually de-correlating (pre-whitening) at least two or more biopotential signals; and a repetitive estimating section 25 for performing iterative estimation (referential independent component analysis) in order to extract a fetal electrocardiogram signal of the designated lead type using the reference signal.

When the biopotential signal input from the maternal-signal removing section 3 is, e.g., x=(xi), i=1 through n, x is de-correlated in the pre-whitening section 24 and becomes a biopotential signal x1=(x1i), i=1 through n, which is input to the repetitive estimating section 25. Iterative estimation, which is the primary procedure in ICA with references, is performed in the repetitive estimating section 25. The subscript "j" of this repetitive estimating section 25 indicates that estimation has been repeated j times (j=1 through K, where K is any integer equal to or greater than 5; K=30 in the present example).

Iterative estimation is performed in the following sequence. The biopotential signal is weighted using wj=(Wji) (where i=1 through n), and the addition result is designated as yj. wj is slightly modified, and wj+1 is calculated so that the fourth-order cumulant of the correlation yjr of yj and the reference signal r is reduced. This procedure is repeated, and wj, yj is calculated so that the fourth-order cumulant of the correlation yjr is minimized (see the learning-algorithm section 26 of FIG. 5. The yj at this point is the fetal electrocardiogram signal that uses r as the reference series. The initial W value w1=(W1i), i=1 through n can be arbitrarily assigned.

Specifically, wj+1=(Wj+1i) (i=1 through n) after j+1 iterations is estimated using Equation 1:

$$Wj+1i = E(\phi(yj) \times 1j)/E(\phi(yj)yj), \quad \text{[Mathematical Formula 1]}$$
$$yj = \sum_{i=1}^{n} Wji \times 1i$$

$\phi(yj)=(yjr)^L$, L is an integer from 1 to 3, r is the reference signal, and E(*) is the average value during the measurement period.

The ICA with references of the present example involves the correlation of the weighted biopotential signal and the reference signal of the designated induction type having a maximum cumulant of the fourth or second order, and may involve a iterative estimation algorithm so that the absolute value of the weighting of the biopotential signal is 1.

Figure 6:
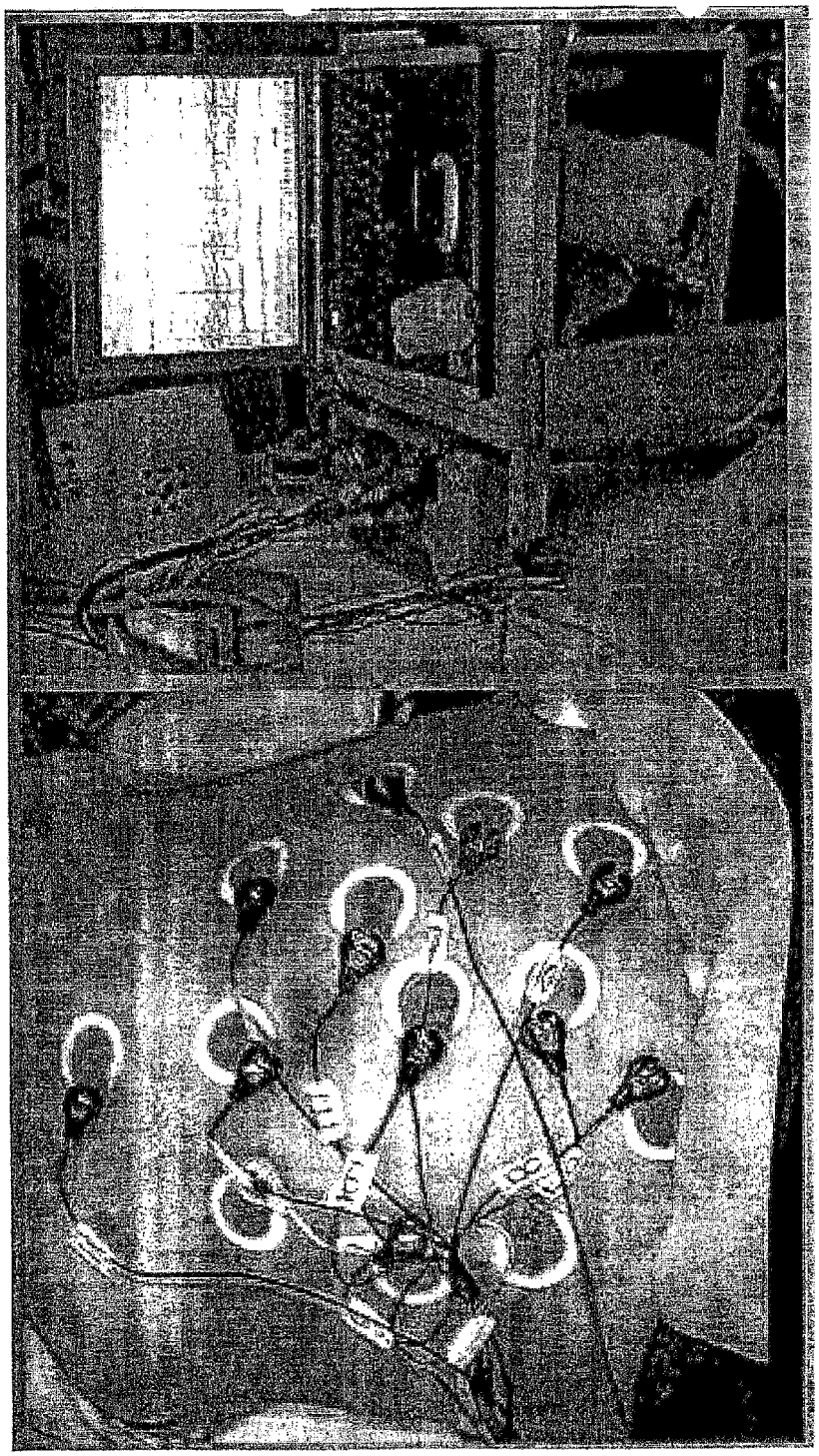
FIG. 6 shows photographs of the electrocardiogram signal-processing device and the circumstances of implementation.
Figure 7:
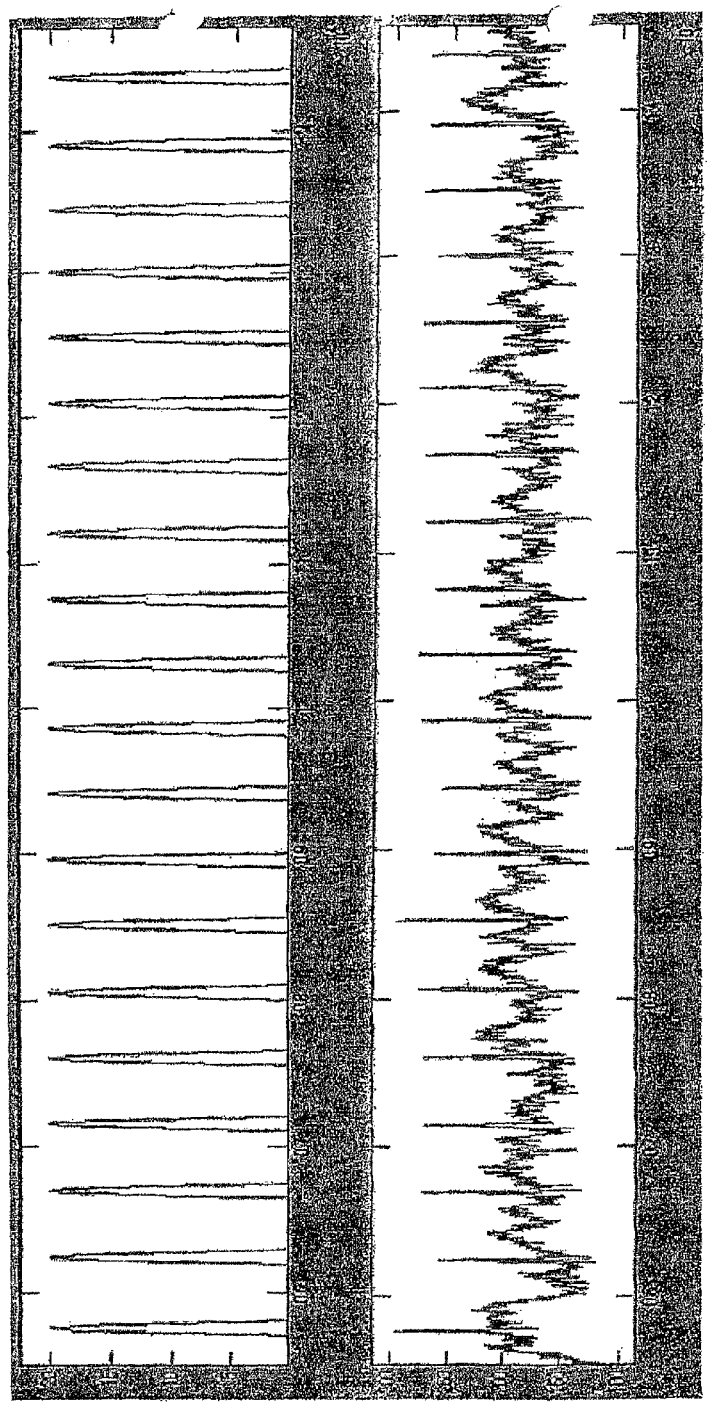
FIG. 7 shows waveforms of a fetal electrocardiogram displayed on a monitor.

FIG. 6 shows photographs of the electrocardiogram signal-processing device A and of the circumstances of implementation when a plurality of the electrodes E are attached to the mother's body 1. FIG. 7 shows an example of a fetal electrocardiogram waveform displayed on the monitor 6 of the electrocardiogram signal-processing device A. It can be seen that P-waves and T-waves can be properly extracted using only an approximate timing function as a reference.

FIGS. 8(a)-8(e) show a comparison of results from conventional independent component analysis (natural gradient) and from two types of referential independent component analysis. Electrodes (scalp electrodes) were attached to the head of a fetus during delivery in a state in which a part of the head of the fetus was exposed outside the uterus and inside the vagina. A direct-induction fetal electrocardiogram was measured over the course of one hour, and a fetal electrocardiogram induced at abdomen of the mother's body was measured simultaneously. An ideal reference series (optimal reference signal), in which an ideal timing was completely harmonized to an R-wave, and a random reference signal, in which the timing was randomly changed ±0.1 seconds, were used for the reference signal. Analysis was performed 10 times a minute and was correlated with the data resulting from the scalp electrodes during each interval.

Figure 8A:
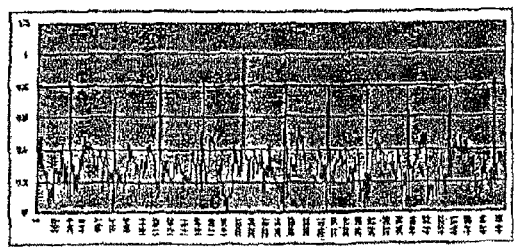
FIGS. 8(a)-8(e) are diagrams that show a comparison of the results of conventional independent component analysis and of the referential independent component analysis of the present invention.
Figure 8B:
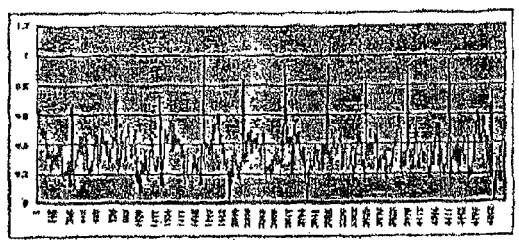
Figure 8C:
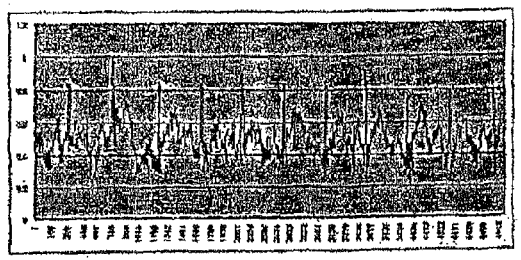
Figure 8D:
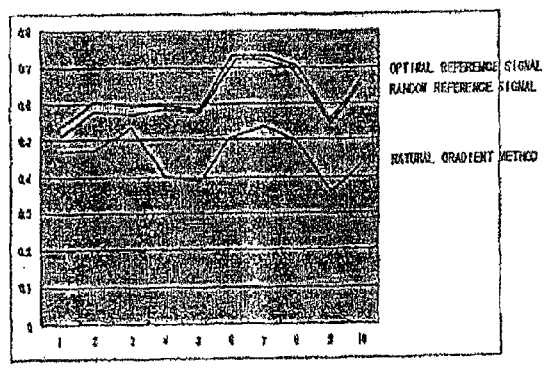
Figure 8E:
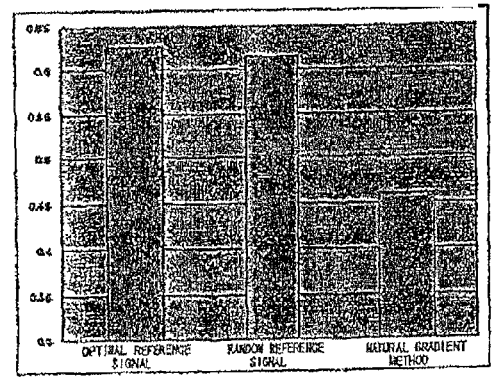

FIG. 8(a) shows extraction results using the random reference series. FIG. 8(b) shows analysis results using the conventional natural gradient method. FIG. 8(c) shows the waveform of the scalp-electrode electrocardiogram during the same interval. FIG. 8(d) shows a graph in which the variation over 10 correlations is seen. The results using the two referential independent component analysis methods display substantially identical precision, which is higher in all cases than the natural gradient method. FIG. 8(e) is a bar graph comparing the average values of 10 correlations. The results in which the two referential independent component analysis methods were used display substantially identical precision, which is significantly higher than the natural gradient method.

The electrocardiogram signal-processing device A of the present example allows a fetal electrocardiogram signal to be non-invasively extracted using the electrodes E attached to the abdomen of the mother's body 1 without damaging the mother's body 1 or the fetus 1b, and also allows extraction regardless of the position or age in weeks of the fetus 1b. The fetal electrocardiogram signal can be extracted without measurement being limited to the time of delivery or other such periods.

The reference signal used in the electrocardiogram signal-processing device A of the present example is based on the heartbeat period of the fetus 1b detected by the ultrasound sensor S, and ICA with references is used to separate and extract the fetal electrocardiogram signal from the biopotential signal detected by the electrodes E, whereby a fetal electrocardiogram signal of the designated lead type (R-wave, P-wave, T-wave) can be actively extracted.

After the maternal electrocardiogram signal, which is the primary source of noise, has been removed in the electrocardiogram signal-processing device A of the present example, the fetal electrocardiogram signal to be determined by repetitive ICA with references is retrieved directly from the biopotential signal. Therefore, electromyogram noise, 50-Hz high-frequency noise, and noise due to other signal sources of similar probability distributions or frequency distributions can be effectively separated, and a fetal electrocardiogram signal can be actively extracted online at high speed.

In the electrocardiogram signal-processing device A of the present example, fetal electrocardiogram signals can be actively extracted online at high speed with high detection sensitivity for not only R-waves, but P-waves and T-waves. A fetal electrocardiogram signal of any lead type can be extracted using the reference signal, and fetal electrocardiogram signals can be actively extracted online at high speed.

Unlike in conventional methods, only the signal to be determined is directly extracted in the electrocardiogram signal-processing device A of the present example, and therefore sequences for investigating the signal extraction order or searching for the fetal electrocardiogram signal in the extracted signal are not necessary, and active extraction is possible online at high speed. The fetal electrocardiogram signal can be directly recovered from the biopotential signal using the correlation with the reference signal as a key after pre-processing for removing the electrocardiogram signal of the mother's body 1, and therefore the effects of the maternal electrocardiogram signal of the mother's body 1 do not readily remain in the signal, and a fetal electrocardiogram signal can be actively extracted online at high speed.

In the electrocardiogram signal-processing device A of the present example, the iterative estimation of independent component analysis includes cases where the reference signal is a constant, and therefore a great deal of ambiguity is allowable in the reference signal. The target fetal electrocardiogram signal can be accurately extracted as long as the robustness of independent component analysis is obtained and the reference signal displays the strongest probability-distribution correlation with the target fetal electrocardiogram signal.

A fetal electrocardiogram waveform based on the fetal electrocardiogram signal can be shown on the monitor 6 and analyzed in the electrocardiogram signal-processing device A of the present example in order to measure the state of health of the fetus 1b. R-wave changes, P-wave changes, and T-wave changes in the extracted fetal electrocardiogram signal can be investigated, whereby fetal arrhythmia or myocardial ischemia can be diagnosed. The fetal electrocardiogram signal can be displayed and analyzed in order to measure the fetal cardiac rate and display fluctuations in the heartbeat using changes in the R-wave interval obtained from the extracted fetal electrocardiogram signal.

Using the electrocardiogram signal-processing device A of the present example, a high-precision detection algorithm can be provided for detecting composite fetal electrocardiogram waves containing not only R-waves but P-waves and T-waves from the multi-channel signal induced from the abdomen of the mother's body, and an online fetal-electrocardiogram detecting system based on a portable polygraph recording system can also be provided.

An example of the present invention was described above using the drawings, but the specific configuration is not limited to these examples, and any changes or additions that do not deviate from the scope of the main concepts of the present invention are also included in the present invention.

For example, the electrocardiogram-signal processing method of the present invention, in which a fetal electrocardiogram signal is separated and extracted from a biopotential signal using independent component analysis on the basis of a reference signal, was used in an electrocardiograph for detecting a biopotential signal using electrodes in the aforedescribed example, but the present invention is not limited to this case and may also be applied to a magnetocardiograph or the like for measuring the slight magnetic signal produced by the heart and using back calculation to determine the electrocardiogram signal from the measured magnetic signal.

The fetal heartbeat-period generating signal for generating the reference signal was detected in the aforedescribed example using an ultrasound sensor in which ultrasound waves were employed and which was attached to the abdomen of the mother's body, but the present invention is not limited to this case. A sensor (detector) for detecting the fetal heartbeat-period generating signal using heart sounds, magnetism, or other means may also be used.

A maternal electrocardiogram signal removing step was performed in the aforedescribed example in order to remove beforehand the maternal electrocardiogram signal from the biopotential signal input from the electrodes, whereby the fetal electrocardiogram signal was more readily extracted from the biopotential signal, but the present invention is not limited to this case. The fetal electrocardiogram signal may also be directly extracted in the fetal electrocardiogram-signal extracting step from the biopotential signal input from the electrodes without performing the maternal electrocardiogram signal removing step.

In the aforedescribed example, a plurality of biopotential signals were averaged and an averaged biopotential signal was generated in the averaged biopotential-signal generating step, and a plurality of maternal electrocardiogram signals were averaged and an averaged maternal electrocardiogram signal was generated in the averaged maternal electrocardiogram-signal generating step, whereby the fetal electrocardiogram signal was more readily extracted from the biopotential signal in the fetal electrocardiogram-signal extracting step, but the present invention is not limited to this case. A maternal electrocardiogram signal that has not been averaged may also be removed in the maternal electrocardiogram signal removing step from a biopotential signal that has not been averaged, without performing the averaged biopotential-signal generating step or the averaged maternal electrocardiogram-signal generating step.

In the aforedescribed example, weighting was performed using the least-squares method, with a dynamic average (*5) value being used for the maternal electrocardiogram signal, and a transformation vector was created. However, the present invention is not limited to this case. A transformation vector may be created and an average value may also be determined using a method other than the method of least squares.

A re-montaging step was performed in the aforedescribed example for reorganizing the bipolar terminals of the electrodes into an optimal combination, but the present invention is not limited to this case. The fetal electrocardiogram signal may also be extracted from the biopotential signal in the fetal electrocardiogram-signal extracting step without performing the re-montaging step, or the re-montaging step may be performed only when a good fetal electrocardiogram signal is not obtained in the fetal electrocardiogram-signal extracting step, and the fetal electrocardiogram signal may then be re-extracted in the fetal electrocardiogram-signal extracting step.

A template signal conforming to the designated induction type was selected from a plurality of template signals stored in advance in the reference-signal generating means in the aforedescribed example, and a reference signal was generated in the reference-signal generating step, but the present invention is not limited to this case. A template signal of the necessary lead type may also be generated using another means for generating template signals without storing template signals in the reference-signal generating means. Alternatively, when the fetal electrocardiogram signal is extracted in the fetal electrocardiogram-signal extracting step, this fetal electrocardiogram signal may be fed back to the reference-signal generating means, whereby a template signal can be generated on the basis of the extracted fetal electrocardiogram signal, and a reference signal can be generated based on this template signal.

INDUSTRIAL APPLICABILITY

The electrocardiogram signal-processing device of the present invention can be applied not only as a fetal monitor (fetal electrocardiograph), which performs a central role in obstetric medicine, but may also be applied in fetal arrhythmia diagnosis, fetomaternal correlation measurements, and a variety of other obstetric fields.

The invention claimed is:

1. An electrocardiogram signal processing method for extracting an electrocardiogram signal of a fetus from a biopotential signal containing electrocardiogram signals of the fetus and of a pregnant mother's body inputted via electrodes attached to the pregnant mother's body, comprising:

a reference signal generating step for generating a reference signal, on the basis of a heartbeat period generating signal inputted from a detector for detecting a heartbeat period signal of the fetus; and a fetal electrocardiogram signal extracting step for separating and extracting the fetal electrocardiogram signal of a designated lead type from the biopotential signal, which was inputted from said electrodes, by using independent component analysis with references, which performs iterative computational estimations using, per computation, the reference signal generated in said reference signal generating step.

2. The electrocardiogram signal processing method according to claim 1, wherein said heartbeat period generating signal is an ultrasound signal inputted from an ultrasound sensor that can be attached to the mother's body.

3. The electrocardiogram signal processing method according to claim 1, further comprising:

a maternal electrocardiogram signal removing step for removing, from the biopotential signal inputted from said electrodes, a primary component of an electrocardiogram of the mother's body, which is based on the electrocardiogram signal of the mother's body inputted via maternal electrodes attached primarily to a chest part of the mother's body.

4. The electrocardiogram signal processing method according to claim 3, further comprising:

an averaged biopotential signal generating step for averaging a plurality of biopotential signals inputted from said electrodes that are attached so that the biopotential signals obtained at a plurality of different locations on the mother's body have spatially independent vector components, and for generating an averaged biopotential signal; and an averaged maternal electrocardiogram signal generating step for averaging a plurality of electrocardiogram signals of the mother's body inputted from the maternal electrodes, which are attached so that the biopotential signals obtained at a plurality of different locations primarily on the chest part of the mother's body have spatially independent vector components, and for generating an averaged maternal electrocardiogram signal, wherein in said maternal electrocardiogram signal removing step, the primary component of the electrocardiogram of the mother's body, which is based on the averaged maternal electrocardiogram signal generated in said averaged maternal electrocardiogram signal generating step, is removed from the averaged biopotential signal generated in said averaged biopotential signal generating step.

5. The electrocardiogram signal processing method according to claim 3, wherein in said maternal electrocardiogram signal removing step, a transformation vector is created on the basis of weighting using the least-squares method from the averaged maternal electrocardiogram signal generated in said averaged maternal electrocardiogram signal generating step and/or an averaged maternal electrocardiogram signal generated by averaging a plurality of temporally repeating units included in the electrocardiogram signal of the mother's body inputted from one maternal electrode; and the primary component of the electrocardiogram of the mother's body is removed on the basis of the maternal electrocardiogram signal estimated using said created transformation vector.

6. The electrocardiogram signal processing method according to claim 1, further comprising:

a re-montaging step for reorganizing bipolar terminals of said electrodes in an optimal combination on the basis of inputted information concerning a position of the fetus in order to perform at least said fetal electrocardiogram signal extracting step.

7. The electrocardiogram signal processing method according to claim 1, wherein in said reference signal generating step, a value of the fetal heartbeat period is specified on the basis of said heartbeat period generating signal;

a template signal that conforms to the designated lead type is selected from a plurality of template signals; and the reference signal is generated on the basis of the selected template signal so that a period value will be identical to said specified value of the fetal heartbeat period.

8. An electrocardiogram signal processing device for extracting an electrocardiogram signal of a fetus from a biopotential signal containing electrocardiogram signals of the fetus and of a pregnant mother's body inputted via electrodes attached to the pregnant mother's body, comprising:

a heartbeat period generating signal inputting section for inputting a heartbeat period generating signal of the fetus;

a reference signal generator for generating a reference signal on the basis of the heartbeat period generating signal inputted from said heartbeat period signal inputting section; and a fetal electrocardiogram signal extractor for separating and extracting the fetal electrocardiogram signal of a designated lead type from the biopotential signal, which was inputted from said electrodes, by using independent component analysis with references, which performs iterative computational estimations using, per computation, the reference signal generated by said reference signal generator.

9. The electrocardiogram signal processing device according to claim 8, wherein the heartbeat period generating signal inputted to said heartbeat period generating signal inputting section is an ultrasound signal inputted from an ultrasound sensor that can be attached to the mother's body.

10. The electrocardiogram signal processing device according to claim 8, further comprising:

a maternal electrocardiogram signal remover for removing, from the biopotential signal inputted from said electrodes, a primary component of an electrocardiogram of the mother's body, which is based on the electrocardiogram signal of the mother's body inputted via maternal electrodes attached primarily to a chest part of the mother's body.

11. The electrocardiogram signal processing device according to claim 10, further comprising:

an averaged biopotential signal generator for averaging a plurality of biopotential signals inputted from said electrodes, which are attached so that the biopotential signals obtained at a plurality of different locations on the mother's body have spatially independent vector components, and for generating an averaged biopotential signal; and an averaged maternal electrocardiogram signal generator for averaging a plurality of electrocardiogram signals of the mother's body inputted from the maternal electrodes, which are attached so that the biopotential signals obtained at a plurality of different locations primarily on the chest part of the mother's body have spatially independent vector components, and for generating an averaged maternal electrocardiogram signal, wherein in said maternal electrocardiogram signal remover, the primary component of the electrocardiogram of the mother's body, which is based on the averaged maternal electrocardiogram signal generated by said averaged maternal electrocardiogram signal generator, is removed from the averaged biopotential signal generated by said averaged biopotential signal generator.

12. The electrocardiogram signal processing device according to claim 10, wherein in said maternal electrocardiogram signal remover, a transformation vector is created on the basis of weighting using the least-squares method from the averaged maternal electrocardiogram signal generated by the averaged maternal electrocardiogram signal generator and/or an averaged maternal electrocardiogram signal generated by averaging a plurality of temporally repeating units included in the electrocardiogram signal of the mother's body inputted from one maternal electrode; and the primary component of the electrocardiogram of the mother's body is removed on the basis of the maternal electrocardiogram signal estimated using said created transformation vector.

13. The electrocardiogram signal processing device according to claim 8, further comprising:

a re-montager for reorganizing bipolar terminals of said electrodes in an optimal combination on the basis of inputted information concerning a position of the fetus, in order to at least separate and extract the fetal electrocardiogram signal using said fetal electrocardiogram signal extractor.

14. The electrocardiogram signal processing device according to claim 8, wherein in said reference signal generator, a value of the fetal heartbeat period is specified on the basis of said heartbeat period generating signal;

a template signal that conforms to the designated lead type is selected from a plurality of previously stored template signals; and the reference signal is generated on the basis of said selected template signal so that a period value will be identical to said specified value of the fetal heartbeat period.

* * * * *